US012272025B2

(12) United States Patent
Schleyer et al.

(10) Patent No.: US 12,272,025 B2
(45) Date of Patent: Apr. 8, 2025

(54) LIVE DISPLAY OF PET IMAGE DATA

(71) Applicant: Siemens Medical Solutions USA, Inc., Malvern, PA (US)

(72) Inventors: Paul Schleyer, Knoxville, TN (US); Inki Hong, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 260 days.

(21) Appl. No.: 17/634,577

(22) PCT Filed: Jan. 14, 2020

(86) PCT No.: PCT/US2020/013423
§ 371 (c)(1),
(2) Date: Feb. 11, 2022

(87) PCT Pub. No.: WO2021/145856
PCT Pub. Date: Jul. 22, 2021

(65) Prior Publication Data
US 2022/0265237 A1     Aug. 25, 2022

(51) Int. Cl.
*G06T 5/50*     (2006.01)
*A61B 6/00*     (2024.01)
(Continued)

(52) U.S. Cl.
CPC ............... *G06T 5/50* (2013.01); *A61B 6/037* (2013.01); *A61B 6/486* (2013.01); *A61B 6/5223* (2013.01);
(Continued)

(58) Field of Classification Search
CPC ....... A61B 6/5223; A61B 6/037; A61B 6/486; G06T 11/005; G06T 15/20; G06T 2200/04; G06T 2211/40
See application file for complete search history.

(56) References Cited

U.S. PATENT DOCUMENTS

| | | | |
|---|---|---|---|
| 2008/0107229 A1* | 5/2008 | Thomas | A61B 6/037 378/207 |
| 2009/0123048 A1 | 5/2009 | Leroux et al. | |
| 2011/0022375 A1* | 1/2011 | Odille | G01R 33/5611 703/13 |

(Continued)

FOREIGN PATENT DOCUMENTS

| | | |
|---|---|---|
| CN | 103519813 | 1/2014 |
| CN | 104107065 | 10/2014 |

(Continued)

OTHER PUBLICATIONS

Vandenberghe, Stefaan et al, "Fast Construction of 3D time-of-flight PET data by axial rebinning and transverse mashing", Physics in Medicine and Biology, 51, 2006, 1603-1621, 20 pp.

(Continued)

*Primary Examiner* — Margaret G Webb

(57) ABSTRACT

A system and method include localization of a first frame of positron emission tomography data acquired by an imaging device to a first frame of Cartesian data, generation of a first Cartesian image volume based on the first frame of Cartesian data, display of the first Cartesian image volume, localization of a second frame of positron emission tomography data acquired by the imaging device to a second frame of Cartesian data, generation of a second Cartesian image volume based on the second frame of Cartesian data, and display of the combined Cartesian image volume.

20 Claims, 9 Drawing Sheets

(51) Int. Cl.
  *A61B 6/03* (2006.01)
  *G06T 11/00* (2006.01)
  *G06T 15/20* (2011.01)

(52) U.S. Cl.
  CPC ............ *G06T 11/005* (2013.01); *G06T 15/20* (2013.01); *G06T 2200/04* (2013.01)

(56) References Cited

U.S. PATENT DOCUMENTS

| | | | |
|---|---|---|---|
| 2012/0070057 A1 | 3/2012 | Zhang et al. | |
| 2017/0249758 A1* | 8/2017 | Mistretta | A61B 6/504 |
| 2019/0008598 A1* | 1/2019 | Frimer | G16H 30/40 |
| 2019/0339403 A1* | 11/2019 | Bai | G01T 1/2985 |
| 2020/0294285 A1* | 9/2020 | Song | G06T 5/50 |
| 2021/0007682 A1* | 1/2021 | Chmeissani Raad | A61B 6/4266 |

FOREIGN PATENT DOCUMENTS

| | | |
|---|---|---|
| CN | 109472786 | 3/2019 |
| WO | 2006111869 A2 | 10/2006 |

OTHER PUBLICATIONS

Matej, Samuel et al, Analytic TOF PET reconstruction algorithm within Direct data partitioning framework, Institute of Physics and Engineering in Medicine, Physics in Medicine & Biology 61 3365-3386, 2016, 23 pp.

International Search Report received in corresponding PCT Application No. PCT/US2020/013423, dated Sep. 18, 2020.

Wu Zhenzhou et al: "New research advances in non-Cartesian parallel MRI reconstruction", Chinese journal of scientific instrument, vol. 38, No. 8, Aug. 15, 2017.

* cited by examiner

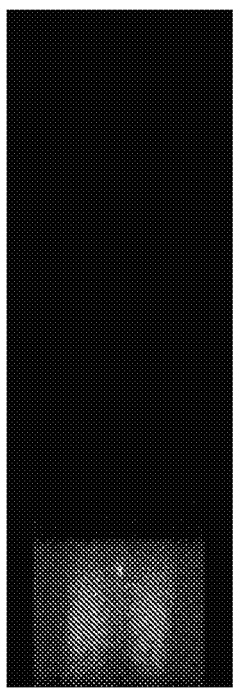 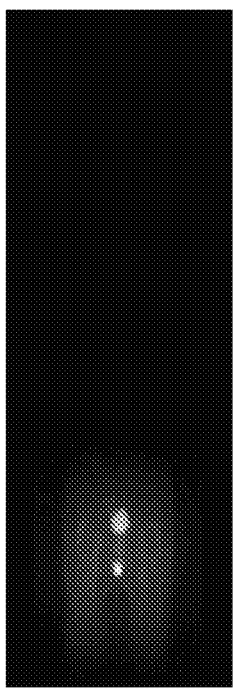 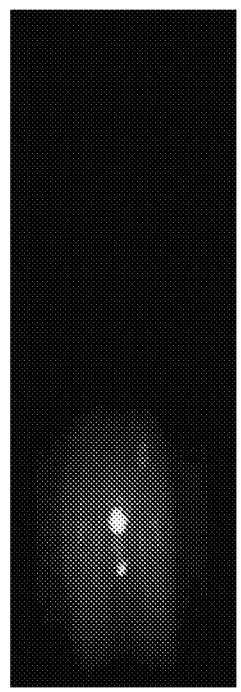 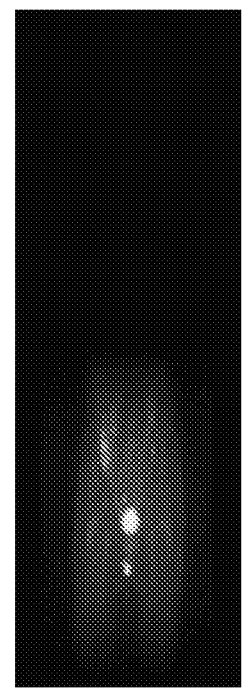
FIG. 7A  FIG. 7B  FIG. 7C  FIG. 7D
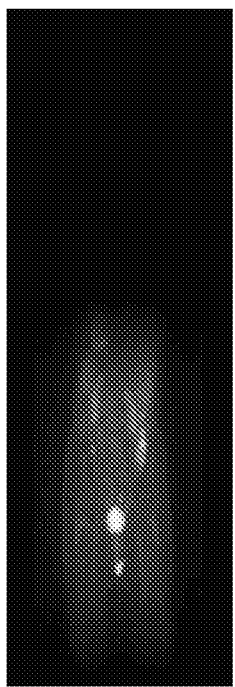 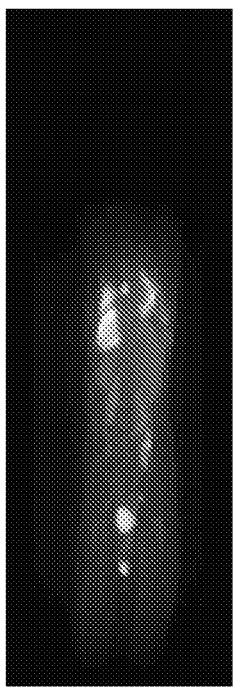 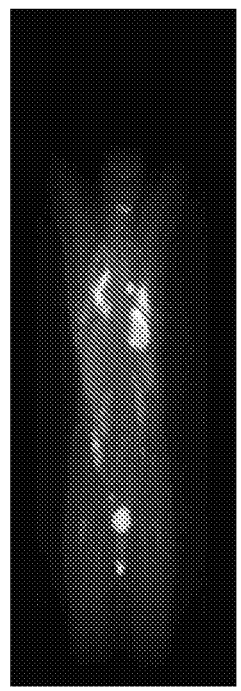 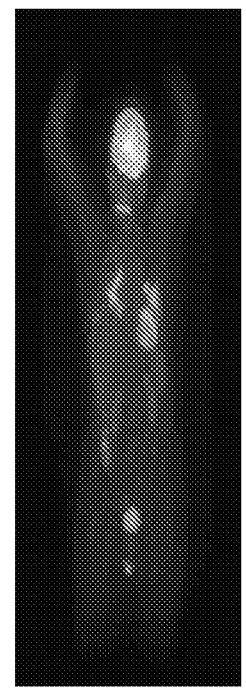
FIG. 7E  FIG. 7F  FIG. 7G  FIG. 7H

LIVE DISPLAY OF PET IMAGE DATA

BACKGROUND

According to conventional positron-emission-tomography (PET) imaging, a radioisotope tracer is initially injected into a patient body. Inside the body, the radioisotope tracer emits positrons which annihilate with electrons to produce gamma rays. A detector system located outside the body detects the emitted gamma rays and records the associated annihilation events in a sinogram or as list-mode data. A three-dimensional Cartesian image may then be reconstructed based on the sinogram/list-mode data.

Reconstruction is time and resource-consuming. A reconstructed image is only available for viewing well after completion of a PET scan. Such delay limits the ability to use PET imaging in conjunction with interventional procedures. Moreover, current techniques do not provide suitable indications of temporal tracer distribution. Systems are desired to improve the timeliness and of usefulness of images generated based on PET data.

BRIEF DESCRIPTION OF THE DRAWINGS

FIGS. 7A through 7H comprise two-dimensional depictions of three-dimensional image volumes generated from PET data according to some embodiments;

DETAILED DESCRIPTION

The following description is provided to enable any person in the art to make and use the described embodiments and sets forth the best mode contemplated for carrying out the described embodiments. Various modifications, however, will remain apparent to those in the art.

Generally, some embodiments provide direct localization of PET data to Cartesian spatial locations in order to generate Cartesian image data for display. Additional PET data is acquired and is also projected to Cartesian spatial locations in order to generate additional Cartesian image data. This additional Cartesian image data is combined with the already-displayed Cartesian image data and an image is displayed based on the combined image data.

Some embodiments may therefore provide near real-time images during PET scanning. Such images may allow for live interventional procedures based on contemporaneously-acquired PET data.

According to some embodiments, the additional PET data is acquired from a different body region than the region from which the prior PET data was acquired. Combination of the additional Cartesian image data with the already-displayed Cartesian image data may therefore allow display of a field of view of an entire moving scan, with regions thereof being gradually "filled-in" as the scan progresses.

In some embodiments, the combination of the sets of Cartesian image data may be time-dependent. For example, the currently-displayed image data may be weighted less than the newly-generated Cartesian image data in the above-described combination of currently-displayed image data with newly-generated Cartesian image data. As new PET data frames are acquired and Cartesian image data generated therefrom is combined with a currently-displayed image, the weighting serves to decrease the prominence of earlier-acquired PET data in each subsequently-displayed combined frame.

The combination of sets of Cartesian image data may also or alternatively be spatially-dependent. For example, the combination may weight image data of certain regions (e.g., far outside of a region of interest) less than image data of other regions.

Figure 1:
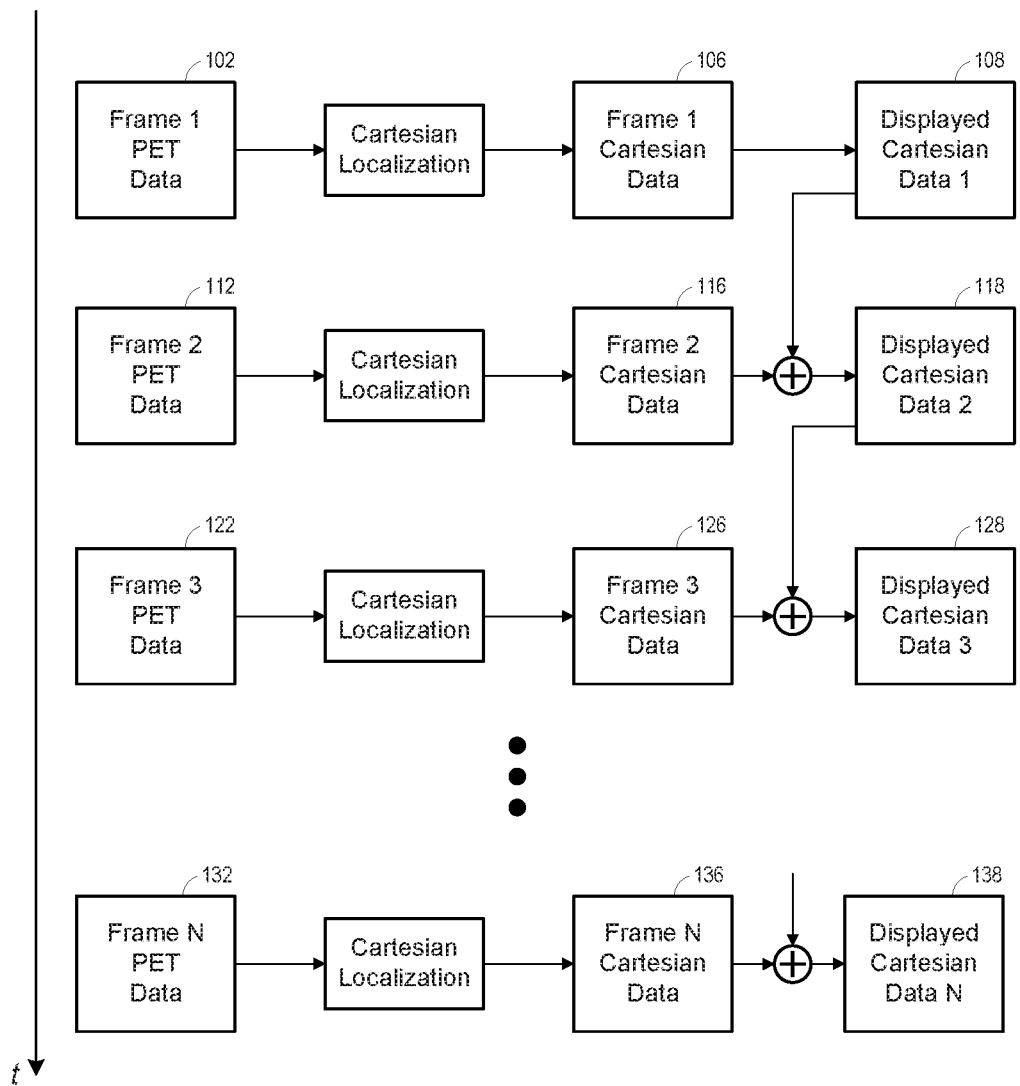
FIG. 1 illustrates a process to generate three-dimensional image volumes from PET data according to some embodiments.

FIG. 1 illustrates generation of three-dimensional image volumes from PET data according to some embodiments. Progressing down time axis t, PET data 102 through 132 represent successively-acquired frames of PET data.

Generally, and as is known in the art, radioactive decay of a PET tracer injected into a body compound generates positrons, which eventually encounter electrons and are annihilated thereby. Annihilation produces two gamma photons which travel in approximately opposite directions. An annihilation event is identified when two detectors disposed on opposite sides of the body detect the arrival of two oppositely-travelling gamma photons within a particular coincidence time window.

Because the two gamma photons travel in approximately opposite directions, the locations of the two detectors determine a Line-of-Response (LOR) along which the annihilation event occurred. Time-of-flight (TOF) PET additionally measures the difference between the arrival times of the two gamma photons arising from each annihilation event. Modern PET scanners are capable of measuring the difference in arrival times of each photon with enough accuracy to provide an indication of the spatial location along the LOR where the positron annihilation occurred.

Each frame of PET data 102 through 132 may comprise list-mode data describing each coincidence event, or LOR, detected within a particular time period associated with the frame, along with TOF information for each event. Conventionally, the LOR and TOF of each event are put into a list-mode stream as the events are detected, and a new "frame" of data is established each time the defined frame duration elapses.

In some embodiments, PET data 102 through 132 is stored in data arrays referred to as sinograms. A sinogram indicates the angle versus the displacement of each LOR. Each sinogram stores the location of the LOR of each coincidence event such that all the LORs passing through a single point in the volume trace a sinusoid curve in the sinogram. Each sinogram includes one row containing the LOR for a particular azimuthal angle φ. Multiple events detect along a same LOR are histogrammed to preserve the successive events.

Figure 2:
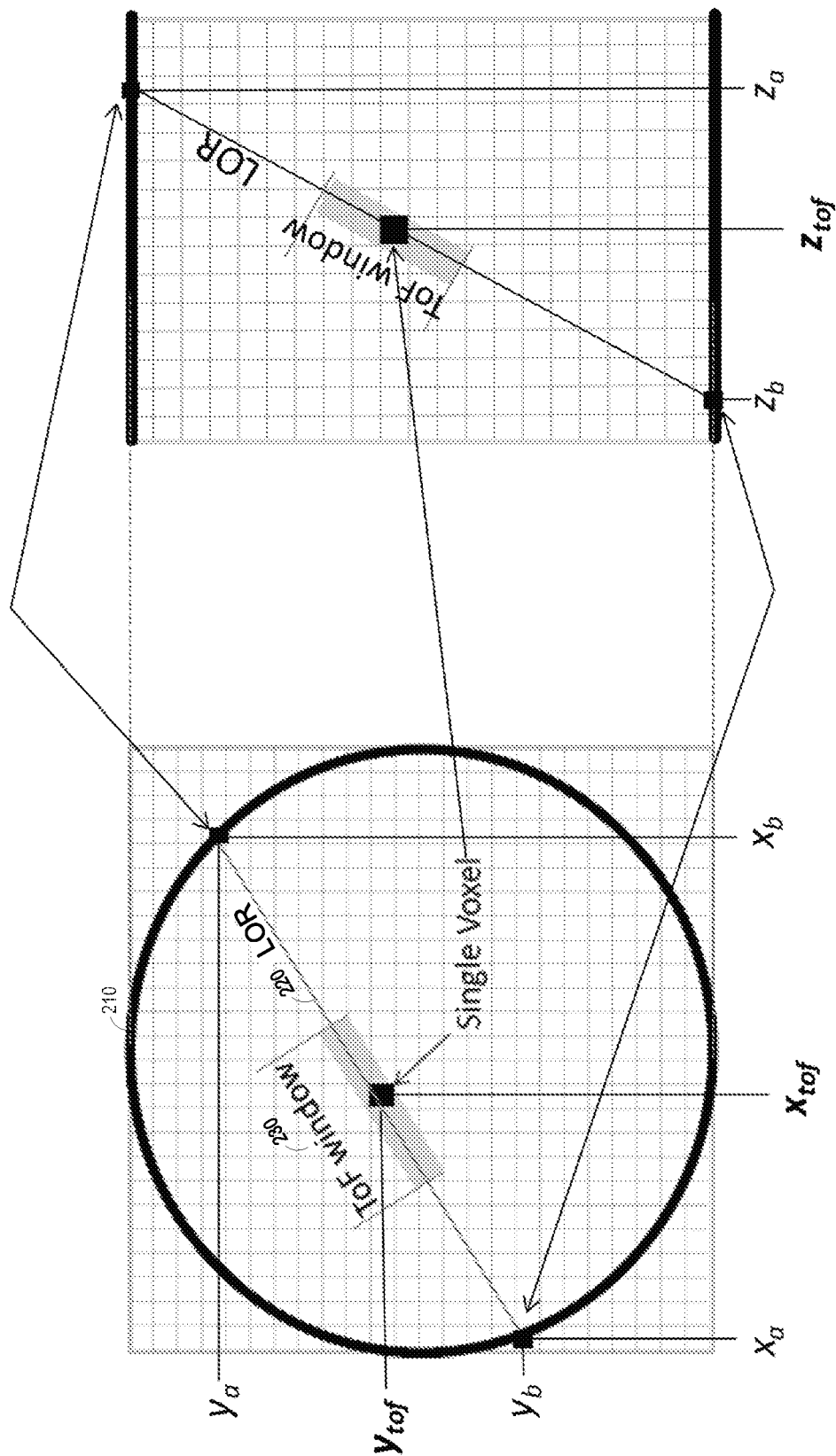
FIG. 2 illustrates localization of an event from detector space to Cartesian coordinates according to some embodiments.

As depicted in FIG. 1, each of frames 102 through 132 is subjected to a Cartesian localization to generate corresponding frames of Cartesian data 106 through 136. Localization from list-mode TOF PET data to Cartesian data may proceed according to any process that is or becomes known. FIG. 2 illustrates localization of an event from detector space to Cartesian coordinates according to some embodiments.

FIG. 2 shows detector ring 210 composed of gamma photon detectors. It will be assumed that an annihilation event occurs along LOR 220, resulting in the generation of two oppositely-travelling gamma photons which are detected by detectors located at detector coordinates, $x_a$, $y_a$ and $x_b$, $y_b$. Due to the respective arrival times of the gamma photons at the detectors, it can be determined that the annihilation event occurred along LOR 220 within TOF window 230. According to some embodiments, it is assumed that the annihilation event occurred at the voxel located along LOR 220 and at the center of TOF window 230.

Localization of a TOF list-mode frame to a Cartesian frame may include localizing each annihilation event to a Cartesian coordinate. For example, the LOR of the annihilation event may be considered as a pair of crystals spatially located at $\vec{P_a}$ and $\vec{P_b}$ and a TOF value that describes the spatial offset, $\delta_{3D}$, of the annihilation event from the LOR center. The spatial location of the estimated annihilation event $\vec{P}$ may then be calculated as:

$$P = \frac{\vec{P_a} + \vec{P_b}}{2} + \frac{\vec{P_a} - \vec{P_b}}{L_{3D}} \cdot \delta_{3D}$$

where $L_{3D}$ is the distance between the two crystals a and b, $$L_{3D} = \| \vec{P_a} - \vec{P_b} \|$$

This may be repeated continuously for each LOR of a frame, to accumulate a volumetric representation of the activity distribution as the LORs are processed. Each event may be corrected for attenuation by weighting its contribution to the Cartesian data by a CT-derived correction factor for the given LOR.

The above process occurs for each subsequently-acquired frame of PET data. However, as shown in FIG. 1, displayed Cartesian data 118 is a combination of displayed Cartesian data 108 and Cartesian data 116 generated based on PET data 112. Similarly, displayed Cartesian data 128 is a combination of displayed Cartesian data 128 and Cartesian data 126 generated based on PET data 122. As described above, techniques for combining the Cartesian may vary among embodiments, producing various results.

According to some embodiments, each frame of Cartesian data 106 through 136 may be considered a histogram which is initialized to 0 at a frame start time. As new detector-pair events are collected in a frame of PET data, each event is localized to a Cartesian coordinate along the LOR at the center of the TOF window. This Cartesian coordinate is incremented in the Cartesian frame (i.e., histogram). At the frame end time, the Cartesian frame is combined with the currently-displayed Cartesian volume and displayed.

The combined Cartesian data may be displayed as navigable, quantitative Cartesian volumes (i.e., manually-selectable transaxial, sagittal, and coronal slices), as sagittal and coronal maximum intensity projection (MIP) views, or as a single rotating MIP.

Figure 3:
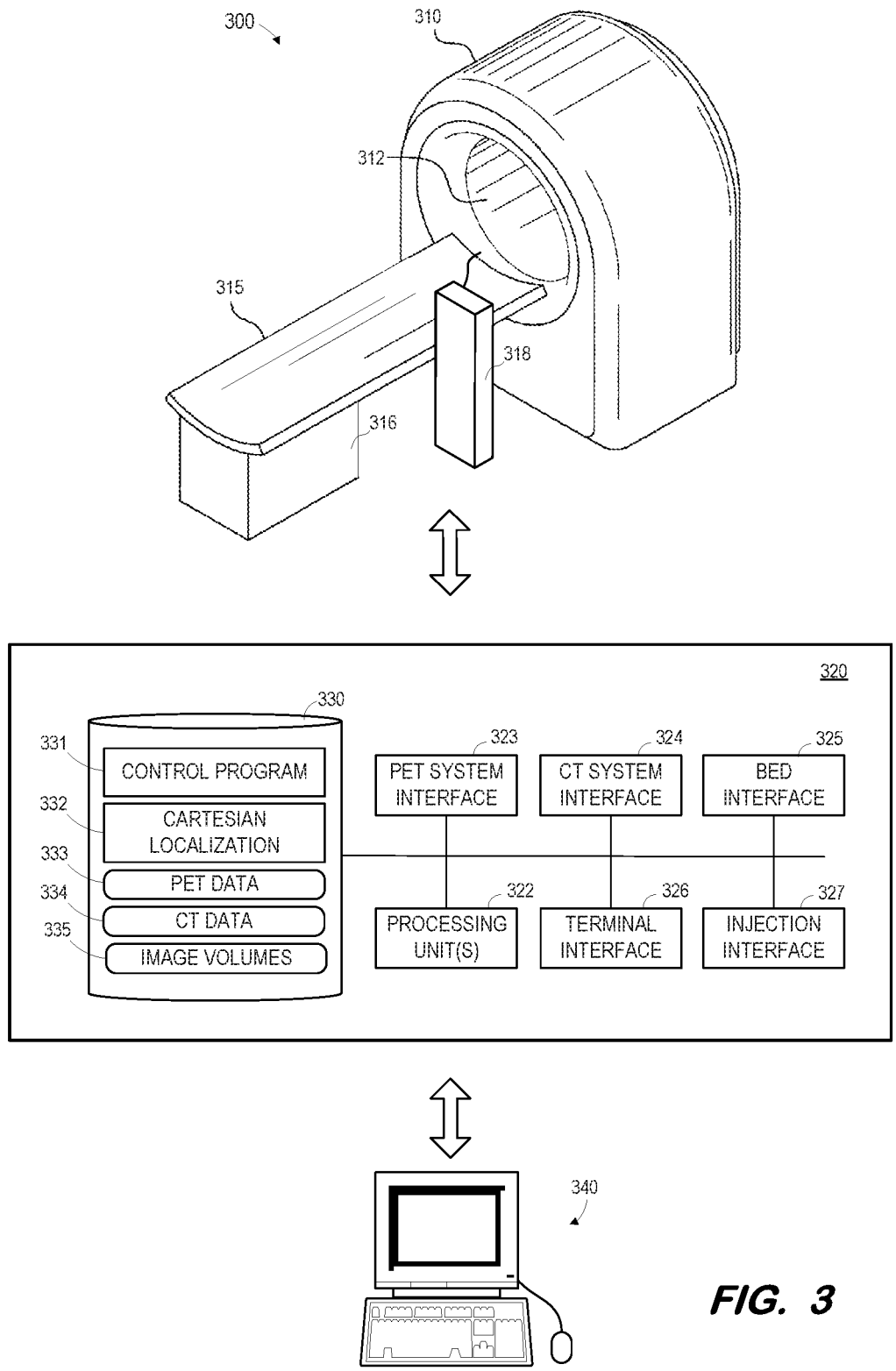
FIG. 3 is a block diagram of a PET/CT imaging system according to some embodiments.

FIG. 3 is a block diagram of a PET/CT imaging system 300 to execute one or more of the processes described herein. Embodiments are not limited to system 300.

System 300 includes gantry 310 defining bore 312. As is known in the art, gantry 310 houses PET imaging components for acquiring PET image data and CT imaging components for acquiring CT image data. The CT imaging components may include one or more x-ray tubes and one or more corresponding x-ray detectors as is known in the art.

The PET imaging components may include any number or type of detectors (e.g., silicon photo-multipliers (SiPM)) in any configuration as is known in the art. The detectors are associated with a slice thickness (spatial resolution) such that the components are capable of independently imaging two slices separated by a distance greater than or equal to the slice thickness. The slice thickness (e.g., 2.0 mm) corresponds to resolution of the detectors.

Injection system 318 may operate to deliver calibrated injections of rubidium, fluorodeoxyglucose (FDG), iodine, or other radioisotopes to a patient before and/or during a PET scan. In some embodiments, injection system 318 is incorporated into gantry 310. Injection system 318 may support a wired or wireless communications link with control system 320 for receiving information specifying dosage, injection protocol and scan delay.

Bed 315 and base 316 are operable to move a patient lying on bed 315 into and out of bore 312 before, during and after imaging. In some embodiments, bed 315 is configured to translate over base 316 and, in other embodiments, base 316 is movable along with or alternatively from bed 315.

Movement of a patient into and out of bore 312 may allow scanning of the patient using the CT imaging elements and the PET imaging elements of gantry 310. Such scanning may proceed based on scanning parameters such as scan ranges and corresponding scanning speeds. Bed 315 and base 316 may provide continuous bed motion and/or step-and-shoot motion during such scanning according to some embodiments.

Control system 320 may comprise any general-purpose or dedicated computing system. Accordingly, control system 320 includes one or more processing units 322 configured to execute processor-executable program code to cause system 320 to operate as described herein, and storage device 330 for storing the program code. Storage device 330 may comprise one or more fixed disks, solid-state random-access memory, and/or removable media (e.g., a thumb drive) mounted in a corresponding interface (e.g., a USB port).

Storage device 330 stores program code of control program 331. One or more processing units 322 may execute control program 331 to, in conjunction with PET system interface 323, bed interface 325, and injection interface 327, control hardware elements to inject a radioisotope into a patient, move the patient into bore 312 past PET detectors of gantry 310, and detect annihilation events occurring within the patient. The detected events may be stored in memory 330 as PET data 333, which may comprise list-mode data and/or sinograms.

One or more processing units 322 may also execute control program 331 to, in conjunction with CT system interface 324, cause a radiation source within gantry 310 to emit radiation toward a body within bore 312 from different projection angles, and to control a corresponding detector to acquire two-dimensional CT data. The CT data may be acquired substantially contemporaneously with the PET data as described above, and may be stored as CT data 334. Such CT data 334 may be used for attenuation correction of contemporaneously-acquired PET data 333 as is known in the art. In this regard, control program 331 may also be executed to reconstruct PET data 333 of a PET scan into three-dimensional slices using any reconstruction algorithm that is or becomes known.

One or more processing units 322 may execute Cartesian localization program 332 to assist in the generation of Cartesian image volumes 335 based on respective frames of PET data 333. Cartesian image volumes 335 may include combined image volumes as described herein.

PET images, CT images and/or image volumes 335 may be transmitted to terminal 340 via terminal interface 326. Terminal 340 may comprise a display device and an input device coupled to system 320. Terminal 340 may display the PET images, CT images, and/or image volumes 335. Terminal 340 may receive user input for controlling display of the data, operation of system 300, and/or the processing described herein. In some embodiments, terminal 340 is a separate computing device such as, but not limited to, a desktop computer, a laptop computer, a tablet computer, and a smartphone.

Each component of system 300 may include other elements which are necessary for the operation thereof, as well as additional elements for providing functions other than those described herein. Each functional component described herein may be implemented in computer hardware, in program code and/or in one or more computing systems executing such program code as is known in the art. Such a computing system may include one or more processing units which execute processor-executable program code stored in a memory system.

Figure 4:
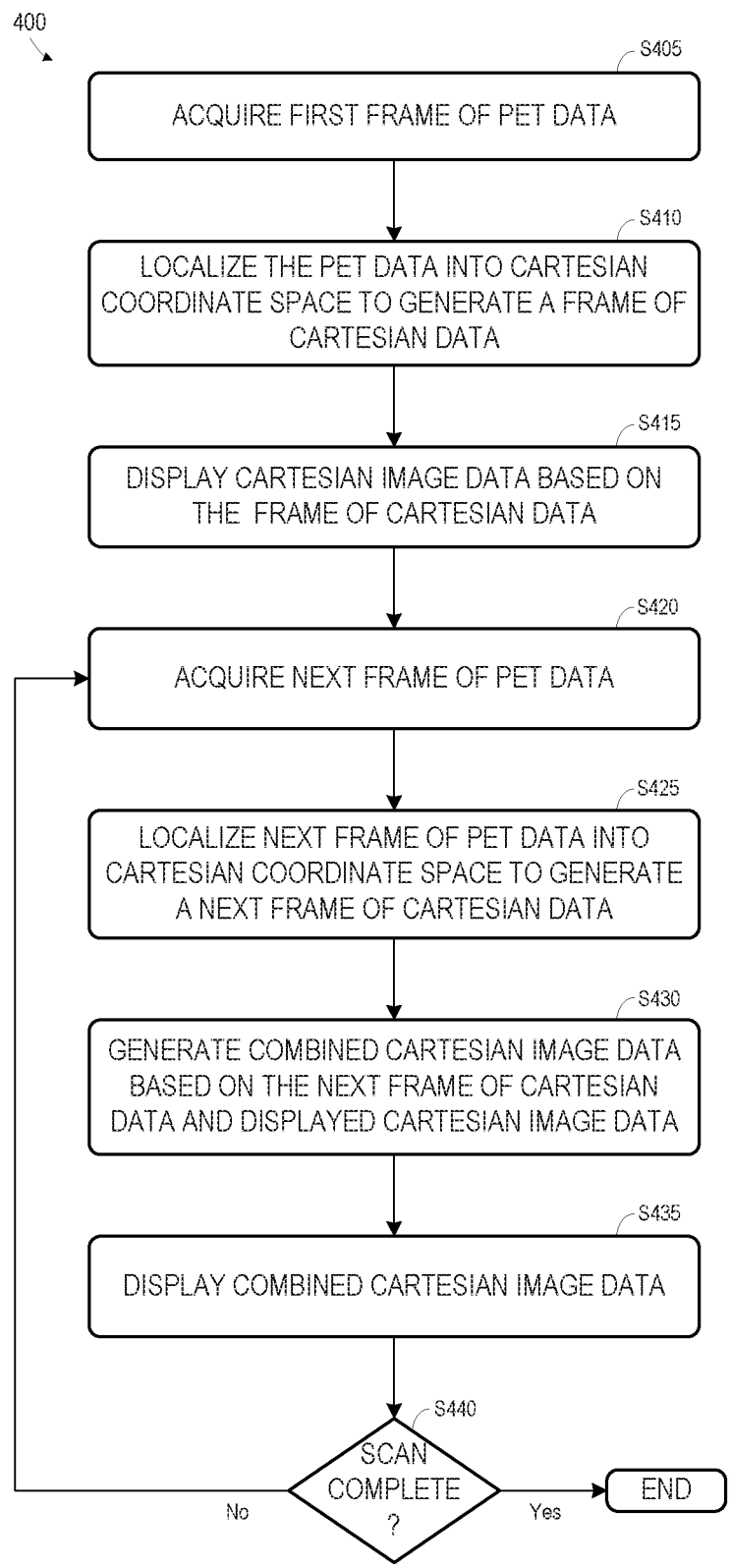
FIG. 4 comprises a flow diagram of a process to generate three-dimensional image volumes from PET data according to some embodiments.

FIG. 4 comprises a flow diagram of process 400 to generate three-dimensional image volumes from PET data according to some embodiments. Flow diagram 400 and other processes described herein may be executed using any suitable combination of hardware and software. Software program code embodying these processes may be stored by any non-transitory tangible medium, including a fixed disk, a volatile or non-volatile random-access memory, a DVD, a Flash drive, and a magnetic tape. Embodiments are not limited to the examples described below.

A first frame of PET data is initially acquired at S405. The PET data may be acquired by a conventional static PET scan after injection of a radioisotope tracer into a subject volume (e.g., a patient) as is known in the art. According to some embodiments, the data acquired by a PET scanner is list-mode data as described above.

Next, at S410, the PET data is localized into a Cartesian coordinate space to generate a frame of Cartesian data. As described above, localization of a particular event to three-dimensional Cartesian space is based on the locations of the detectors which absorbed the coincident gamma photons of the event, and the TOF data of the event. The frame of Cartesian data may comprise a histogram such that the value associated with a particular Cartesian coordinate may be directly related to the number of PET events which are localized to that coordinate.

Cartesian image data is displayed at S415 based on the frame of Cartesian data. As mentioned above, the image data may be displayed using any technique for displaying three-dimensional image data that is or becomes known. A next frame of PET data is acquired at S420. As will be described in more detail below, the next frame of PET data may represent a different imaging region (i.e., a different region of the body) than that of the prior PET frame. The next frame of PET data is localized into a Cartesian coordinate space to generate a next frame of Cartesian data at S425 as described above with respect to S410.

Next, at S430, combined Cartesian image data is generated based on the Cartesian image data displayed at S415 and the Cartesian data generated at S425. Combination at S430 may simply comprise generating image data based on the Cartesian data generated at S425 and adding the generated image data to the Cartesian image data displayed at S415. In some embodiments, the combination of image data may be weighted, where the weight associated with a particular image data value depends on acquisition time, Cartesian coordinate, and/or tracer decay rates.

The combined Cartesian image data is displayed at S435. It is then determined at S440 whether the scan is complete. If not, flow returns to S420 and continues as described above. In particular, a next frame of PET data is acquired at S420 and is localized into a Cartesian coordinate space at S425 to generate a next frame of Cartesian data.

Combined Cartesian image data is generated at S430 based on the most-recently displayed Cartesian image data and the most-recently generated frame of Cartesian data. The new combination of Cartesian image data is displayed at S435. Flow continues to S440 and cycles through S420, S425, S430, S435 and S440 until it is then determined that the scan is complete.

According to some embodiments of process 400, each subsequently-displayed image includes image data of each previously-displayed image. As described below, in some embodiments, the image data of previously-displayed images may fade or eventually be removed entirely as more and more image data is generated and displayed.

Figure 5:
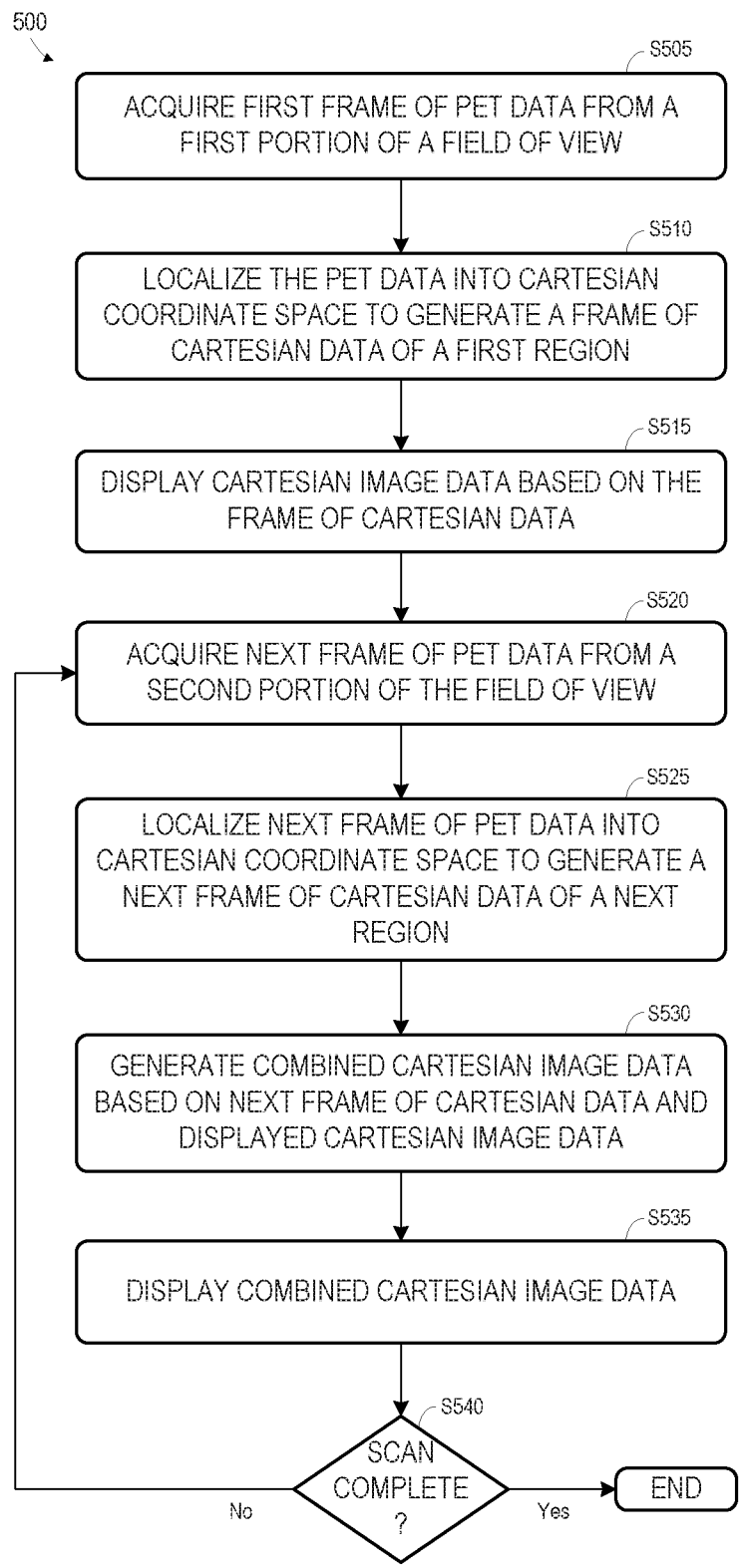
FIG. 5 comprises a flow diagram of a process to generate three-dimensional image volumes from PET data acquired during continuous bed motion according to some embodiments.

FIG. 5 comprises a flow diagram of a process to generate three-dimensional image volumes from PET data acquired during continuous bed motion according to some embodiments.

A first frame of PET data is initially acquired at S505 from a first portion of a field of view. The PET data may be acquired at S505 during continuous bed motion (e.g., 1 mm/s) as is known in the art, in which the field of view is the entire region of the body which passes through the detectors during the scan. The PET data is localized into a Cartesian coordinate space at S510 to generate a frame of Cartesian data, and Cartesian image data is displayed based on the frame of Cartesian data at S515.

A next frame of PET data is acquired from a second portion of the field of view at S420. Due to continuous bed motion, the second portion may be different from the first portion from which the first PET data was acquired. The first portion and the second portion may spatially overlap in some embodiments.

Figure 6:
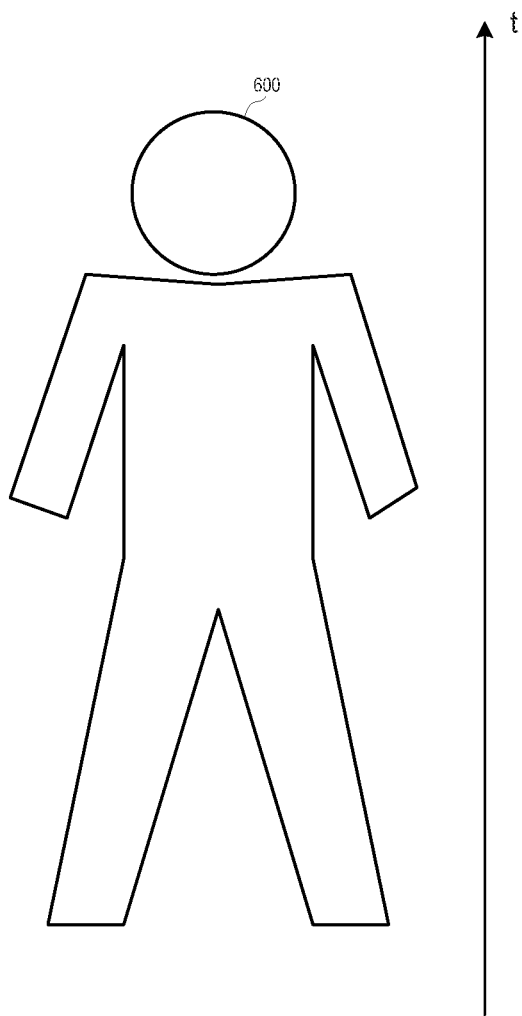
FIG. 6 illustrates performance of a PET scan according to some embodiments.

FIG. 6 illustrates acquisition of PET data during continuous bed motion according to some embodiments. The arrow represents the passage of time during acquisition of PET data, with respect to portions of body 600 from which PET data is acquired during the passage of time. In the illustrated example, acquisition of PET data begins as the lower portions of body 600 are moved past the PET detectors (by virtue of moving bed 315 through bore 312), and continues until the head has moved past the detectors. Each frame of PET data used in process 500 may include data acquired over a specified period of time during the motion.

The next frame of PET data representing the second portion of the field of view is localized into a Cartesian coordinate space to generate a next frame of Cartesian data at S525. Next, at S530, combined Cartesian image data is generated based on the Cartesian image data displayed at S515 and the frame of Cartesian data generated at S525. Since the image data represent different portions of the full axial field of view, combination at S530 may simply comprise generating image data based on the Cartesian data generated at S525 and adding the generated image data to the Cartesian image data displayed at S515.

The combined Cartesian image data is displayed at S535, and flow returns to S520 to continue as described above until scanning is complete. During such cycling, Cartesian image data representing successive portions of the field of view continue to be added to the displayed image data, thereby "completing" the image of the field of view. According to some embodiments, an isotope-dependent decay correction function is applied on-the-fly to newly-generated image data prior to combining the image data with then then-currently-displayed image data. The isotope-dependent decay correction function increases intensity of pixel values based on their associated acquisition time to compensate for isotope decay.

FIGS. 7A through 7H comprise two-dimensional depictions of three-dimensional images generated based on process 500 according to some embodiments. Although only eight images are shown, it should be understood that a full-body PET scan may generate hundreds of PET data frames which may be localized to corresponding frames of Cartesian data.

FIG. 7A may depict first Cartesian image data generated based on a first frame of PET data. FIG. 7B, in turn, may depict Cartesian image generated based on another frame of PET data and added to the first Cartesian image data of FIG. 7A. The additional image data of FIG. 7B may inhabit some of the same Cartesian regions as the FIG. 7A image data. In this regard, localization of PET data to Cartesian data during process 500 accounts for bed movement along the z-axis. For example, the z-position in the full-body field of view at which PET data is acquired is used to determine the z-coordinate of Cartesian data localized therefrom.

As shown, the displayed image "grows" in the z-direction of the scan as additional PET data frames are acquired and localized into Cartesian space. As described above, the intensity of image pixels corresponding to later-acquired frames may be increased based on expected tracer decay in order to normalize intensities within the displayed images. As also described above, the continuously-changing displayed image may comprise manually-selectable transaxial, sagittal, and coronal slices, sagittal and coronal MIP views, or a single rotating MIP, for example.

Figure 8:
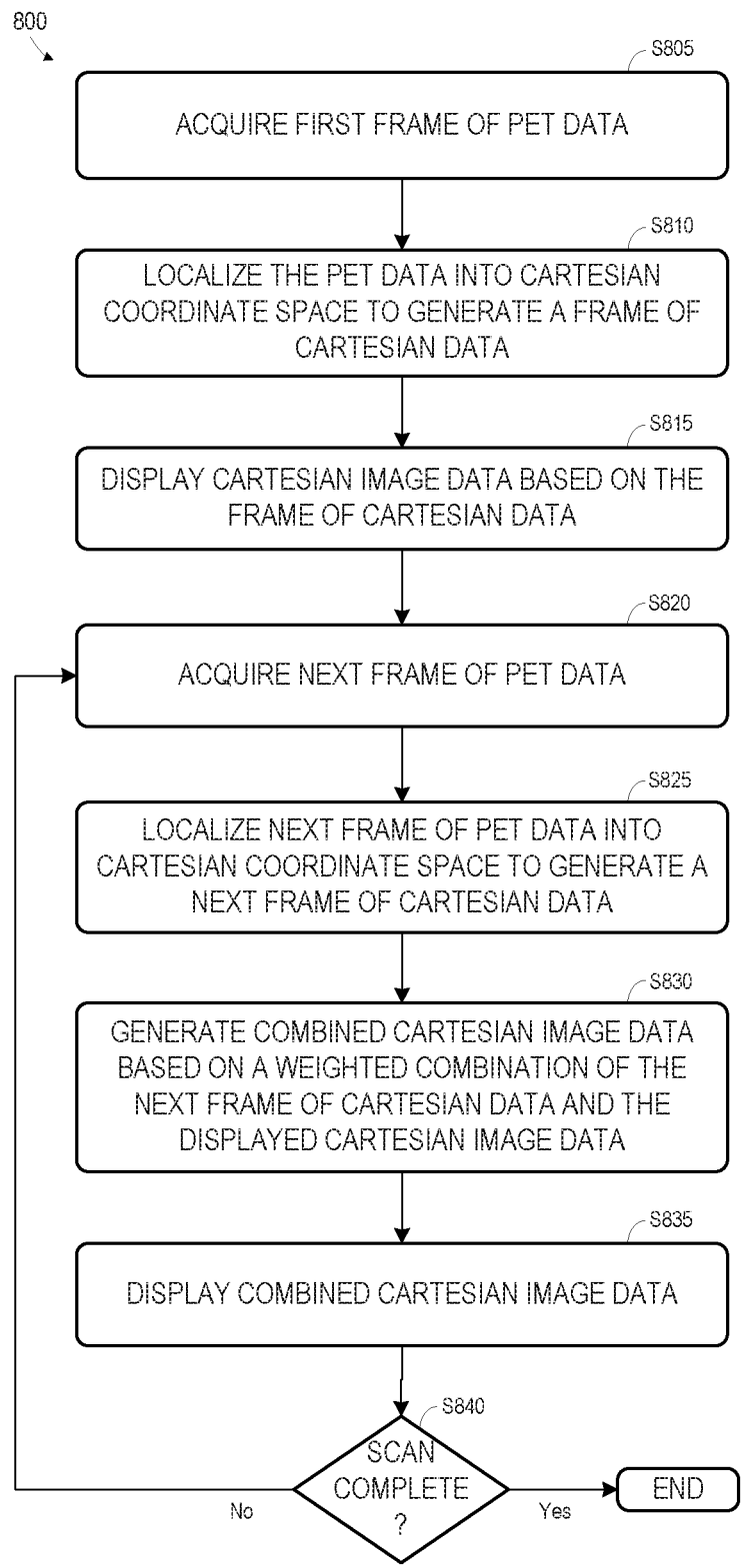
FIG. 8 comprises a flow diagram of a process to generate weighted combinations of past and current image volumes generated from PET data according to some embodiments.
Figure 9A:
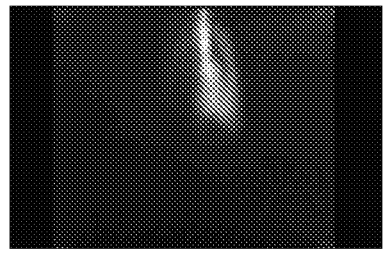
FIGS. 9A through 9D comprise two-dimensional depictions of three-dimensional image volumes generated from past and current image volumes generated from PET data according to some embodiments.
Figure 9B:
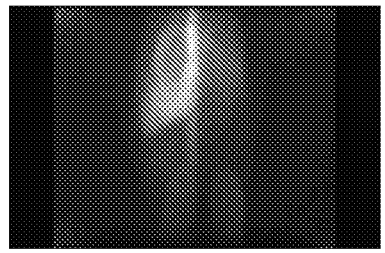
Figure 9C:
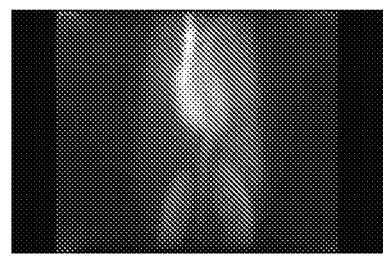
Figure 9D:
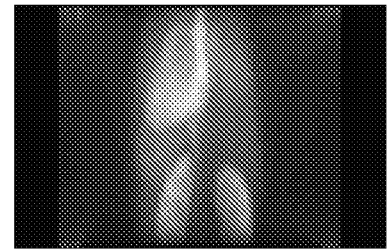
Figure 10A:
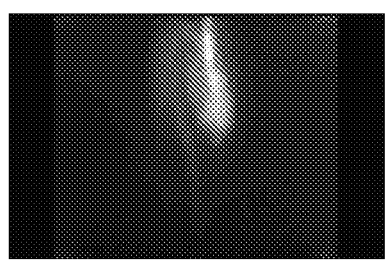
FIGS. 10A through 10D comprise two-dimensional depictions of three-dimensional image volumes generated from past and current image volumes generated from PET data according to some embodiments.
Figure 10B:
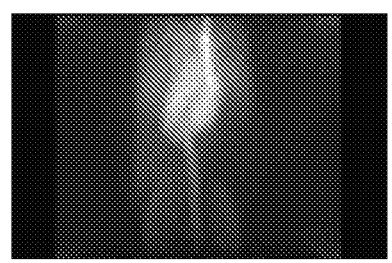
Figure 10C:
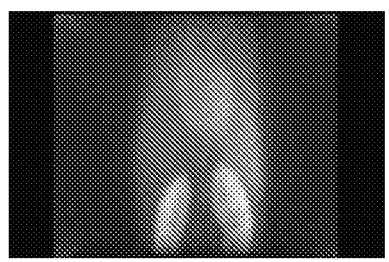
Figure 10D:
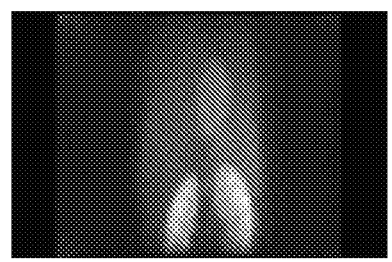

FIG. 8 comprises a flow diagram of process 800 to generate weighted combinations of past and current image volumes generated from PET data according to some embodiments. Steps S805 through S825 may proceed similarly to steps S405 through S425 of process 400. Accordingly, at S825, Cartesian image data generated based on an acquired frame of PET data is currently displayed and a next frame of Cartesian data has been localized based on a next acquired PET data frame.

Next, at S830, combined Cartesian image data is generated based on the currently-displayed image data and the newly-generated (i.e., "next") frame of Cartesian data. As described in detail below, the generation at S830 applies different weights to the displayed image data and to Cartesian image data newly-generated from the next frame of Cartesian data.

In the following description of S830 according to some embodiments, the combined image is denoted $g_t$, the currently-displayed image is denoted $g_{t-1}$, and the newly-generated Cartesian image data is denoted $f_t$. The combined image $g_t$ generated at S830 is a sum of the newly-generated Cartesian image data $f_t$ and a fraction of the currently-displayed image $g_{t-1}$ such that $g_t = \alpha f_t + \beta g_{t-1}$. $\alpha(x, y, z, t)$ is a weighting factor controlling the degree of contribution of image data $f_t$ to the global volume. $\beta(x,y,z,t)$ is a persistence parameter which determines how rapidly events are removed from successive combined images $g_t$.

For example, if $\beta=1$, all prior image data is accumulated in the combined images. If $\beta=0$, the combined image includes only the newest-generated Cartesian image data $f_t$. $\alpha$ and $\beta$ may be held constant, or may be spatially and/or temporally variant to account for known tracer distributions, tracer decay, specific clinical protocols (e.g., myocardial blood flow study), and well-characterized biological processes. Optimal parameters can be calculated analytically or via deep-learning methods.

The combined image is displayed at S835, and flow then cycles from S840 to S820 as described above until the scan is complete.

FIGS. 9A through 9D comprise two-dimensional depictions of three-dimensional image volumes generated at S830 and displayed at S835 according to some embodiments. FIGS. 9A through 9D illustrate an implementation in which $\beta=1$. Accordingly, each successive image includes all the image data of the prior combined image, as well as newly-generated Cartesian image data. In this regard, the implementation of FIGS. 9A through 9D is similar to the implementation depicted in FIGS. 7A through 7H.

FIGS. 10A through 10D comprise two-dimensional depictions of three-dimensional image volumes generated at S830 and displayed at S835 according to some embodiments. In particular, FIGS. 10A through 10D illustrate an implementation in which $\beta=0.9$. Consequently, each successive image includes all 90% of the image data of the prior combined image, as well as the newly-generated Cartesian image data. Due to the application of $\beta$ to successive images, the degree to which particular image data appears in a combined image depends upon the number of combined images which have been generated since the particular image data was generated. For example, for $\alpha=0.1$ and $\beta=0.9$, a third combined image may be generated as $0.9((0.9 \times \text{Image}_1) + \text{Image}_2) + \text{Image}_3 = 0.81 \text{Image}_1 + 0.9 \text{Image}_2 + \text{Image}_3$.

The foregoing diagrams represent logical architectures and processes according to some embodiments, and actual implementations may include more or different components and/or steps arranged in other manners. Moreover, each component or device described herein may be implemented by any number of devices in communication via any number of other public and/or private networks. Two or more of such computing devices may be located remote from one another and may communicate with one another via any known manner of network(s) and/or a dedicated connection. Each component or device may comprise any number of hardware and/or software elements suitable to provide the functions described herein as well as any other functions. For example, any computing device used in an implementation of a system according to some embodiments may include a processor to execute program code such that the computing device operates as described herein.

All systems and processes discussed herein may be embodied in program code stored on one or more non-transitory computer-readable media. Such media may include, for example, a hard disk, a DVD-ROM, a Flash drive, magnetic tape, and solid state Random Access Memory (RAM) or Read Only Memory (ROM) storage units. Embodiments are not limited to any specific combination of hardware and software.

Those in the art will appreciate that various adaptations and modifications of the above-described embodiments can be configured without departing from the claims. Therefore, it is to be understood that the claims may be practiced other than as specifically described herein.

What is claimed is:

1. A system comprising:
an imaging device to:
acquire frames of positron emission tomography data, each frame indicating a respective line-of-response for each of a plurality of detected annihilation events;
a processing system to:
receive a first frame of positron emission tomography data from the imaging device;
generate a first spatial image volume by localizing each annihilation event of the first frame of positron emission tomography data to a Cartesian coordinate based on locations of a pair of crystals of the line-of-response and a time-of-flight value of the annihilation event;
display the first spatial image volume;
while the first spatial image volume is displayed:
receive a second frame of positron emission tomography data from the imaging device;
generate a second spatial image volume by localizing each annihilation event of the second frame of positron emission tomography data to a Cartesian coordinate based on locations of a pair of crystals of the line-of-response and a time-of-flight value of the annihilation event; and
generate a combined spatial image volume based on the first spatial image volume and the second spatial image volume; and
replace the displayed first spatial image volume with display of the combined spatial image volume.

2. A system according to claim 1, wherein first spatial image volume comprises a first portion of a field of view, and wherein the second spatial image volume comprises a second portion of the field of view.

3. A system according to claim 2, wherein generation of the combined spatial image volume comprises modifying the first spatial image volume based on a decay profile of a radioisotope, and addition of the modified first spatial image volume to the second spatial image volume.

4. A system according to claim 1, wherein generation of the combined spatial image volume comprises application of a weight to the first spatial image volume and addition of the weighted first spatial image volume to the second spatial image volume.

5. A system according to claim 4, wherein the weight is based on a difference between an acquisition time of the first frame and a time of the second frame.

6. A system according to claim 4, wherein the weight is spatially-variant.

7. A system according to claim 6, wherein the weight is based on a decay profile of a radioisotope.

8. A method comprising:
receiving a first frame of positron emission tomography data indicating a respective line-of-response for each of a first plurality of detected annihilation events;
generating a first Cartesian image volume by localizing each annihilation event of the first frame of positron emission tomography data to a Cartesian coordinate based on locations of a pair of crystals of the line-of-response and a time-of-flight value of the annihilation event;
displaying the first Cartesian image volume;
while displaying the first Cartesian image volume:
receiving a second frame of positron emission tomography data indicating a respective line-of-response for each of a second plurality of detected annihilation events;
generating a second Cartesian image volume by localizing each annihilation event of the second frame of positron emission tomography data to a Cartesian coordinate based on locations of a pair of crystals of the line-of-response and a time-of-flight value of the annihilation event; and
generating a combined Cartesian image volume based on the first Cartesian image volume and the second Cartesian image volume; and
displaying the combined Cartesian image volume.

9. A method according to claim 8, wherein first Cartesian image volume comprises a first portion of a field of view, and wherein the second Cartesian image volume comprises a second portion of the field of view.

10. A method according to claim 9, wherein generating the combined Cartesian image volume comprises modifying the first Cartesian image volume based on a decay profile of a radioisotope, and adding the modified first Cartesian image volume to the second Cartesian image volume.

11. A method according to claim 8, wherein generating the combined Cartesian image volume comprises applying a weight to the first Cartesian image volume and adding of the weighted first Cartesian image volume to the second Cartesian image volume.

12. A method according to claim 11, wherein the weight is based on a difference between an acquisition time of the first frame of positron emission tomography data and an acquisition time of the second frame of positron emission tomography data.

13. A method according to claim 12, wherein the weight is spatially-variant.

14. A method according to claim 13, wherein the weight is based on a decay profile of a radioisotope.

15. A computing system comprising:
a memory storing processor-executable process steps;
a processing unit to execute the processor-executable process steps to:
for each annihilation event of a first frame of positron emission tomography data, determine a coordinate of a first spatial image volume based on locations of a pair of crystals of the line-of-response and a time-of-flight value of the annihilation event;
display the first spatial image volume;
while the first spatial image volume is displayed:
for each annihilation event of a second frame of positron emission tomography data, determine a coordinate of a second spatial image volume based on locations of a pair of crystals of the line-of-response and a time-of-flight value of the annihilation event;
generate a combined spatial image volume based on the first spatial image volume and the second spatial image volume; and
replace the displayed first spatial image volume with display of the combined spatial image volume.

16. A system according to claim 15, wherein first spatial image volume comprises a first portion of a field of view, and wherein the second spatial image volume comprises a second portion of the field of view.

17. A system according to claim 16, wherein generation of the combined spatial image volume comprises modifying the first spatial image volume based on a decay profile of a radioisotope, and addition of the modified first spatial image volume to the first spatial image volume.

18. A system according to claim 16, wherein generation of the combined spatial image volume comprises application of a weight to the first spatial image volume and addition of the weighted first spatial image volume to the second spatial image volume.

19. A system according to claim 18, wherein the weight is temporally-variant and spatially-variant.

20. A system according to claim 19, wherein generation of the combined spatial image volume comprises modification of the first spatial image volume based on a decay profile of a radioisotope.

\* \* \* \* \*